US011705221B2

(12) United States Patent
Zuo et al.

(10) Patent No.: US 11,705,221 B2
(45) Date of Patent: Jul. 18, 2023

(54) METHOD FOR FORMING HISTORY OF NATURAL GAS ACCUMULATION BY USING CARBON ISOTOPES BY PYROLYSIS EXPERIMENT

(71) Applicant: Chengdu University of Technology, Sichuan (CN)

(72) Inventors: Yinhui Zuo, Chengdu (CN); Ziyun Zheng, Chengdu (CN); Kangnan Yan, Chengdu (CN); Wenting Wu, Chengdu (CN); Meihua Yang, Chengdu (CN)

(73) Assignee: CHENGDU UNIVERSITY OF TECHNOLOGY, Chengdu (CN)

( * ) Notice: Subject to any disclaimer, the term of this patent is extended or adjusted under 35 U.S.C. 154(b) by 500 days.

(21) Appl. No.: 16/940,618

(22) Filed: Jul. 28, 2020

(65) Prior Publication Data

US 2021/0035659 A1    Feb. 4, 2021

(30) Foreign Application Priority Data

Jul. 30, 2019  (CN) .......................... 201910692709.5

(51) Int. Cl.
*G16C 10/00*   (2019.01)
*G16C 20/70*   (2019.01)
(Continued)

(52) U.S. Cl.
CPC .......... *G16C 10/00* (2019.02); *G01N 33/241* (2013.01); *G16C 20/70* (2019.02); *G01N 31/12* (2013.01)

(58) Field of Classification Search
CPC ........ G16C 10/00; G16C 20/70; G16C 20/10; G16C 60/00; G01N 33/241; G01N 31/12;
(Continued)

(56) References Cited

U.S. PATENT DOCUMENTS

| 11,073,504 B2 * | 7/2021 | Mathur | G01N 30/68 |
| 2008/0306695 A1 * | 12/2008 | Fusetti | G01N 33/241 |
| | | | 702/27 |
| 2010/0155078 A1 * | 6/2010 | Walters | G01N 33/241 |
| | | | 703/10 |

OTHER PUBLICATIONS

Wikipedia Contributor (Ed.). (Jul. 24, 2019). Microsoft Excel. Wayback Machine. Retrieved Feb. 2, 2023, from https://web.archive.org/web/20190724085902/https://en.wikipedia.org/wiki/Microsoft_Excel (Year: 2019).*

(Continued)

*Primary Examiner* — Daniel R Miller
*Assistant Examiner* — Eric Sebastian Von Wald
(74) *Attorney, Agent, or Firm* — Crowell & Moring LLP

(57) ABSTRACT

The present invention provides a method for forming a history of natural gas accumulation by using carbon isotopes by a pyrolysis experiment. The method includes: obtaining activation energy distribution and a frequency factor of light carbon methane; carrying out carbon isotope kinetics simulation of natural gas in a study area by using a spreadsheet function of Excel to obtain activation energy, a mass fraction and a frequency factor of heavy carbon methane; establishing a burial history and a thermal history of the study area based on geological data; and combining the activation energy distribution and frequency factor of the heavy carbon methane with the burial history and thermal history of the study area, and establishing an instantaneous curve, a cumulative curve and a stage cumulative curve of natural gas under geological conditions on a geologic time scale.

9 Claims, 2 Drawing Sheets

(51) Int. Cl.
*G01N 33/24* (2006.01)
*G01N 31/12* (2006.01)

(58) Field of Classification Search
CPC ....... G01N 33/0049; G01N 2030/8405; G01N 2223/202; H01J 49/0472; C07C 45/51; C01B 2210/0026; C08F 2500/20
See application file for complete search history.

(56) References Cited

OTHER PUBLICATIONS

Lu, S., Li, J., Xue, H., Chen, F., Xu, Q., Wang, M., et al. (2019). Pyrolytic gaseous hydrocarbon generation and the kinetics of carbon isotope fractionation in representative model compounds with different chemical structures. Geochemistry, Geophysics, Geosystems, 20, 1773-1793. (Year: 2019).*

* cited by examiner

METHOD FOR FORMING HISTORY OF NATURAL GAS ACCUMULATION BY USING CARBON ISOTOPES BY PYROLYSIS EXPERIMENT

RELATED APPLICATION

This application claims priority to Chinese Patent Application No. 201910692709.5, filed with the China National Intellectual Property Administration on Jul. 30, 2019, which is incorporated herein by reference in its entirety.

TECHNICAL FIELD

The present invention belongs to the technical field of geological research, and in particular relates to a method for forming a history of natural gas accumulation by using carbon isotopes by a pyrolysis experiment.

BACKGROUND

In actual geological conditions, the process of natural gas migration and accumulation is extremely complicated. Early static models were built only based on a large amount of measured data, which often led to distorted research results. It has been gradually recognized that the influencing factors of natural gas carbon isotopes include geochemistry and geological processes, which must be comprehensively studied to objectively reveal the natural gas migration and accumulation processes under geological conditions. In order to break the limitation of the static models, a series of kinetic models were established by incorporating the effects of matrix type, thermal maturation, time and accumulation on carbon isotopes based on the essential problem of carbon isotope fractionation.

However, due to the harsh conditions of the kinetics simulation and the complexity of the kinetics simulation process, the application of these models is limited. Therefore, there is an urgent need for a simpler method to quantitatively describe the history of the formation, migration and accumulation of natural gas, which is crucial for natural gas resource evaluation and exploration decision.

SUMMARY

In order to solve the above-mentioned deficiencies in the prior art, the present invention provides a method for forming a history of natural gas accumulation by using carbon isotopes by a pyrolysis experiment. The present invention solves the problem of limited application of the existing static models established only based on thermal simulation experimental data or based on measured carbon isotope data, and simplifies the simulation process of forming a natural gas accumulation history.

To achieve the above objective, the present invention adopts the following technical solutions.

This solution provides a method for forming a history of natural gas accumulation by using carbon isotopes by a pyrolysis experiment, including the following steps:

S1, selecting a kerogen sample for a pyrolysis experiment to obtain activation energy, a mass fraction and a frequency factor of light carbon methane;

S2, carrying out carbon isotope kinetics simulation of natural gas in a study area by using a spreadsheet of Excel based on the activation energy, the mass fraction and the frequency factor of the light carbon methane, to obtain activation energy, a mass fraction and a frequency factor of heavy carbon methane;

S3, establishing a burial history and a thermal history of the study area based on geological data; and S4, combining the activation energy, the mass fraction and the frequency factor of the heavy carbon methane with the burial history and the thermal history of the study area to establish an instantaneous curve, a cumulative curve and a stage cumulative curve of the natural gas under geological conditions to form a history of natural gas accumulation.

Further, step S1 includes the following steps:

S101, selecting a kerogen sample for a pyrolysis experiment to obtain a pyrolysis product of the kerogen sample and a yield thereof; and S102, carrying out hydrocarbon generation kinetics analysis by using KINETICS software based on the pyrolysis product and the yield thereof, to obtain activation energy, a mass fraction and a frequency factor of light carbon methane.

Further, step S2 includes the following steps:

S201: expanding the activation energy and the mass fraction of the light carbon methane, and setting expansion values as initial values of the activation energy and the mass fraction of heavy carbon methane;

S202: calculating a frequency factor of the heavy carbon methane according to the frequency factor of the light carbon methane, where the frequency factor of the heavy carbon methane is expressed as follows:

$$A^{13}C = 1.02 \times A^{12}C$$

where, $A^{13}C$ represents the frequency factor of the heavy carbon methane, and $A^{12}C$ represents the frequency factor of the light carbon methane;

S203, calculating conversion rates and reaction rates of total reaction light carbon methane and heavy carbon methane precursors by the activation energy, the mass fraction and the frequency factor of the light carbon methane and the initial values of the activation energy and mass fraction of the heavy carbon methane and the frequency factor thereof;

S204, calculating a carbon isotope cumulative amount according to the conversion rates and the reaction rates of the total reaction light carbon methane and heavy carbon methane precursors as well as the pyrolysis experiment data, where the carbon isotope cumulative amount is expressed as follows:

$$\delta^{13}C(t) = [R_0 F(t)/F^*(t)/R_{std} - 1]1000$$

$$R_0 = (\delta^{13}C_0/1000 + 1)R_{std}$$

where, $\delta^{13}C(t)$ represents a carbon isotope cumulative amount at time t; $R_0$ represents an initial carbon isotope ratio of the methane precursors; $F(t)$ and $F^*(t)$ represent the conversion rates of the total reaction heavy carbon methane and light carbon methane precursors, respectively; $\delta^{13}C_0$ represents an initial carbon isotope amount; $R_{std}$ represents a standard ratio of Pee Dee Belemnite (PDB);

S205, setting an activation energy difference $\Delta Ea$ between the heavy carbon methane and the light carbon methane as a variable cell in a spreadsheet window of Excel;

S206, obtaining a target value in the spreadsheet function according to a carbon isotope measured amount from the pyrolysis experiment and the carbon isotope cumulative amount, where the target value X is expressed as follows:

$$X = \Sigma_t |\delta^{13}C^*(t) - \delta^{13}C(t)|$$

where, $\delta^{13}C^*(t)$ represents a carbon isotope measured amount at time t, and $\delta^{13}C(t)$ represents a carbon isotope cumulative amount at time t;

S207, establishing a constraint for obtaining the activation energy and mass fraction of the heavy carbon methane; and S208, fitting the target value by using a nonlinear interior point method of Excel according to the constraint; determining whether the target value is close to a preset limit value 0 during the fitting process; if yes, completing the fitting to obtain the activation energy, mass fraction and frequency factor of the heavy carbon methane; otherwise, returning to step S205.

Further, step S203 includes the following steps:

S2031, calculating reaction rate constants of all reaction light carbon methane and heavy carbon methane separately according to the activation energy, the mass fraction and the frequency factor of the light carbon methane and the initial values of the activation energy and the mass fraction of the heavy carbon methane as well as the frequency factor thereof;

S2032, calculating unreacted amounts of all reaction light carbon methane and heavy carbon methane precursors separately according to the activation energy, the mass fraction and the frequency factor of the light carbon methane and the initial values of the activation energy and the mass fraction of the heavy carbon methane as well as the frequency factor thereof;

S2033, calculating conversion rates of all the reaction light carbon methane and heavy carbon methane precursors separately according to the unreacted amounts of the light carbon methane and heavy carbon methane precursors; calculating reaction rates of all the reaction light carbon methane and heavy carbon methane precursors separately according to the conversion rates of the light carbon methane and heavy carbon methane precursors;

S2034, calculating conversion rates and reaction rates of the total reaction light carbon methane and heavy carbon methane precursors separately according to the conversion rates and reaction rates of all the reaction light carbon methane and heavy carbon methane precursors.

Further, in step S2031, the reaction rate constant of each reaction light carbon methane or heavy carbon methane is expressed as follows:

$$k_i = A \exp(-Ea_i/RT)$$

where, $Ea_i$ represents the activation energy of the light carbon methane or the heavy carbon methane; A represents the frequency factor of the light carbon methane or the heavy carbon methane; R represents an ideal gas constant; T represents a temperature; $k_i$ represents a reaction rate constant of i-th reaction light carbon methane or heavy carbon methane; i=1, . . . , n, and n represents a total number of reactants.

Further, in step S2032, the unreacted amount of each reaction light carbon methane or heavy carbon methane precursor is expressed as follows:

$$w_i(t) = \exp\left[-\sum_t \Delta U_i(t)\right]$$

$$\Delta U_i(t) = [U_i(t) - U_i(t-1)]/Hr$$

$$U_i(t) = T(t)A\exp(-Ea_i/RT(t)) \times \left\{1 - \frac{[Ea_i/RT(t)]^2 + a_1[Ea_i/RT(t)] + a_2}{[Ea_i/RT(t)]^2 + b_1[Ea_i/RT(t)] + b_2}\right\}$$

where, $w_i(t)$ represents an unreacted amount of the i-th reaction light carbon methane or heavy carbon methane precursor at time t; $\Delta U_i(t)$ represents an average cumulative amount of a light carbon methane or heavy carbon methane reaction product from time t to time t−1; Hr represents a constant heating rate; $U_i(t)$ represents a cumulative amount of the light carbon methane or heavy carbon methane reaction product at time t; R represents an ideal gas constant; T represents a temperature; $k_i$ represents a reaction rate constant of the i-th reaction light carbon methane or heavy carbon methane; $Ea_i$ represents the activation energy of the light carbon methane or heavy carbon methane; $a_1$, $a_2$, $b_1$ and $b_2$ represent constants for calculating the cumulative amount of the light carbon methane or heavy carbon methane reaction product at time t, $a_1$=2.334733, $a_2$=0.250621, $b_1$=3.330657 and $b_2$=1.681534.

Further, in step S2033, the conversion rate of each reaction light carbon methane or heavy carbon methane precursor is expressed as follows:

$$F_i(t)=f_{oi}[1-w_i(t)]$$

the reaction rate of each reaction light carbon methane or heavy carbon methane precursor is expressed as follows:

$$r_i(t)=k_i(t)[f_{oi}-F_i(t)]$$

where, $F_i(t)$ represents a conversion rate of the i-th reaction light carbon methane or heavy carbon methane precursor at time t; $f_{oi}$ represents a mass fraction of each reaction light carbon methane or heavy carbon methane; $w_i(t)$ represents an unreacted amount of the i-th reaction light carbon methane or heavy carbon methane precursor at time t; $r_i(t)$ represents a reaction rate of the i-th reaction light carbon methane or heavy carbon methane at time t; $k_i(t)$ represents a reaction rate constant of the i-th reaction light carbon methane or heavy carbon methane at time t.

Further, in step S2034, the conversion rate of the total reaction light carbon methane or heavy carbon methane precursor is expressed as follows:

$$F^*(t)=\Sigma F_i(t)$$

$$F(t)=\Sigma F_i(t)$$

the reaction rate of the total reaction light carbon methane or heavy carbon methane precursor is expressed as follows:

$$r^*(t)=\Sigma r_i(t)$$

$$r(t)=\Sigma r_i(t)$$

where, F(t) and F*(t) represent the conversion rates of the total reaction heavy carbon methane and light carbon methane precursors at time t; r(t) and r*(t) represent the reaction rates of the total reaction heavy carbon methane and light carbon methane precursors at time t; $F_i(t)$ represents the conversion rate of the i-th reaction light carbon methane or heavy carbon methane precursor at time t; $r_i(t)$ represents the reaction rate of the i-th reaction light carbon methane or heavy carbon methane at time t.

Further, in step S207, the constraint is:

a sum of the mass fractions $f_{oi}$ of all the reaction heavy carbon methane is set to 1, $f_{oi} \geq 0$, and a range of the activation energy difference $\Delta Ea$ between the reaction heavy carbon methane and the light carbon methane is set to 80-250 J/mol.

Further, in step S4, the established cumulative curve of natural gas under geological conditions is expressed as follows:

$$\delta^{13}C(t)=[R_0F(t)/F^*(t)/R_{std}-1]1000$$

$$R_0=(\delta^{13}C_0/1000+1)R_{std}$$

where, $\delta^{13}C_{cum}(t)$ represents a carbon isotope cumulative amount of natural gas under geological conditions at time t; $R_0$ represents an initial carbon isotope ratio of the methane precursors; $F(t)$ and $F^*(t)$ represent the conversion rates of the total reaction heavy carbon methane and light carbon methane precursors, respectively; $\delta^{13}C_0$ represents an initial carbon isotope amount; $R_{std}$ represents a standard ratio of PDB;

the established instantaneous curve of natural gas under geological conditions is expressed as follows:

$$\delta^{13}C_{inst}(t) = \{R_0 \Sigma r_i(t)/\Sigma r_i^*(t) \times [1-F(t)]/[1-F^*(t)]/R_{std} - 1\}1000$$

$$R_0 = (\delta^{13}C_0/1000 + 1)R_{std}$$

where, $\delta^{13}C_{inst}(t)$ represents a carbon isotope instantaneous amount of natural gas under geological conditions at time t; $R_0$ represents an initial carbon isotope ratio of the methane precursors; $F(t)$ and $F^*(t)$ represent the conversion rates of the total reaction heavy carbon methane and light carbon methane precursors, respectively; $r_i(t)$ and $r_i^*(t)$ represent reaction rates of i-th reaction heavy carbon methane and light carbon methane precursors at time t; $\delta^{13}C_0$ represents an initial carbon isotope amount; $R_{std}$ represents a standard ratio of PDB;

the established stage cumulative curve of natural gas under geological conditions is expressed as follows:

$$\delta^{13}C_{step}(t) = \delta^{13}C_{inst}(t-1) \times \{[F(t)-F(t-1)]/[F^*(t)-F^*(t-1)]\} + \{[F(t)-F(t-1)]/[F^*(t)-F^*(t-1)]-1\}1000$$

where, $\delta^{13}C_{step}(t)$ represents a carbon isotope stage cumulative amount of natural gas under geological conditions at time t; $\delta^{13}C_{inst}(t-1)$ represents a carbon isotope instantaneous amount of natural gas under geological conditions at time t−1, $F(t)$ and $F(t-1)$ respectively represent a conversion rate of the total reaction heavy carbon methane precursor at time t and t−1; $F^*(t)$ and $F^*(t-1)$ respectively represent a conversion rate of the total reaction light carbon methane precursor at time t and t−1.

The present invention has the following beneficial effects:

The present invention uses the spreadsheet function of Excel to perform the carbon isotope kinetics simulation of methane, specifically including: selecting a representative kerogen sample for a pyrolysis experiment to obtain activation energy distribution and a frequency factor for generating light carbon methane; using the spreadsheet function of Excel to perform the carbon isotope kinetics simulation of methane to obtain activation energy distribution and a frequency factor of heavy carbon methane; establishing a burial history and a thermal history of a study area by geological data; combining the activation energy distribution and frequency factor of the heavy carbon methane with the burial history and thermal history of the study area, and establishing an instantaneous curve, a cumulative curve and a stage cumulative curve of natural gas under geological conditions on a geologic time scale. This method provides a new way of recovering the history of natural gas accumulation based on the hydrocarbon generation kinetics. It simply and flexibly to combines the geochemical experiment with the geological conditions and uses basic geochemical parameters to fit the experimental data, and quantitatively simulates the fractionation process of natural gas carbon isotopes under geological conditions, thereby restoring the history of natural gas accumulation. This method breaks the limitation of static models established only based on thermal simulation experimental data or measured carbon isotope data, and improves the accuracy of the natural gas accumulation history. In addition, this method applies to carbon isotope kinetics simulation of natural gas in a wide range of areas, making the history of natural gas accumulation more authentic, reliable and scientific, thus providing an important basis for oil and gas exploration and resource evaluation.

DETAILED DESCRIPTION

The specific implementations of the present invention are described below to facilitate those skilled in the art to understand the present invention, but it should be clear that the present invention is not limited to the scope of the specific implementations. Various obvious changes made by those of ordinary skill in the art within the spirit and scope of the present invention defined by the appended claims should fall within the protection scope of the present invention.

Limited by the simulation conditions and the complex simulation process, the application of the existing carbon isotope kinetics software based on a series of kinetic models is affected. The present invention conducts the carbon isotope kinetics simulation of methane by using a spreadsheet function of Excel. The method of the present invention is simple, and applies to carbon isotope kinetics simulation of natural gas in a wide range of areas, making the history of natural gas accumulation more authentic and reliable.

Figure 1:
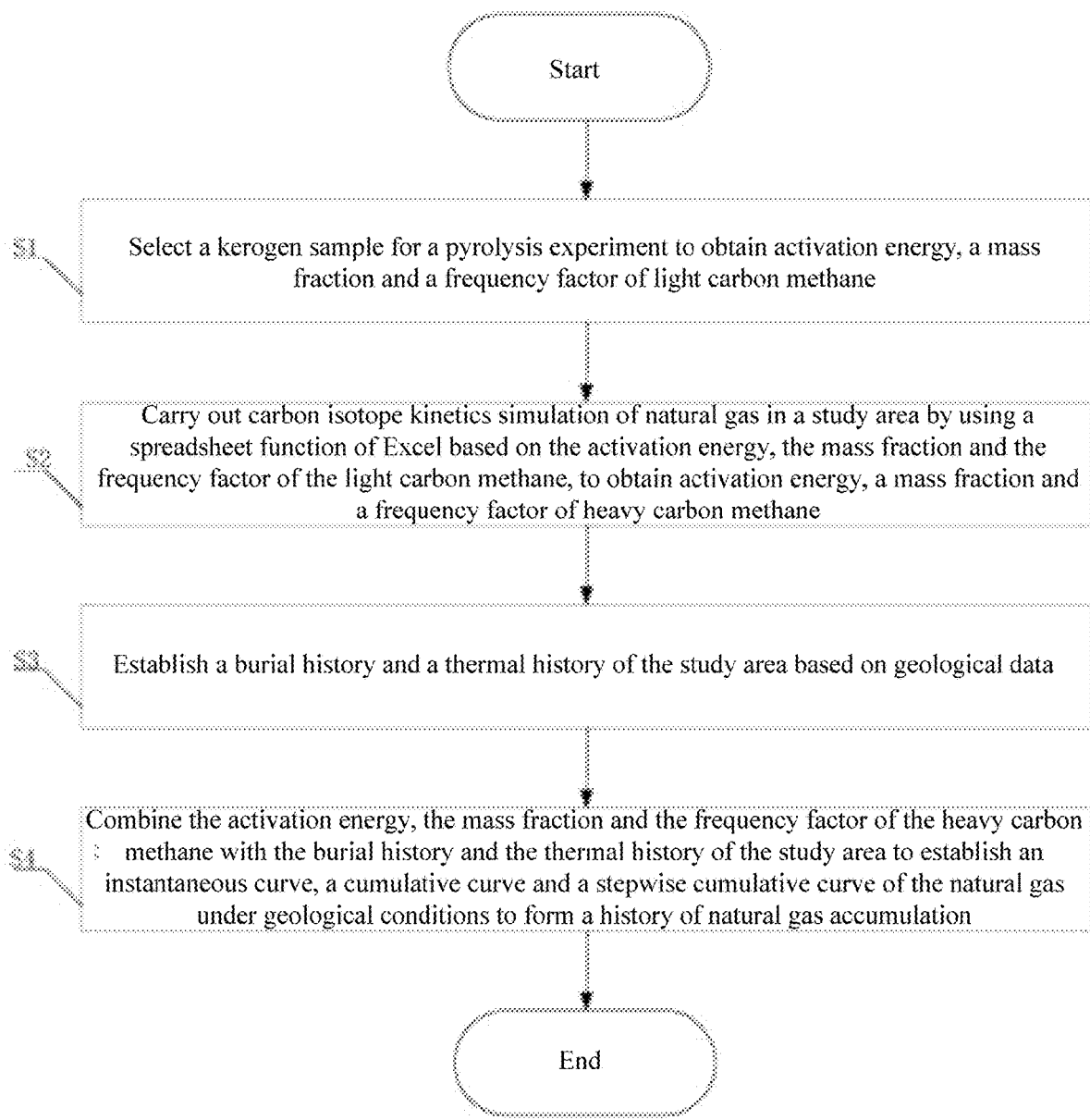
FIG. 1 is a flowchart of a method according to the present invention.

As shown in FIG. 1, the present invention provides a method for forming a history of natural gas accumulation by using carbon isotopes by a pyrolysis experiment, including the following steps:

S1, select a kerogen sample for a pyrolysis experiment to obtain activation energy, a mass fraction and a frequency factor of light carbon methane, including:

S101, select a kerogen sample for a pyrolysis experiment to obtain a pyrolysis product of the kerogen sample and a yield thereof.

S102, carry out hydrocarbon generation kinetics analysis by using KINETICS software based on the pyrolysis product and the yield thereof, to obtain activation energy, a mass fraction and a frequency factor of light carbon methane.

S2, carry out carbon isotope kinetics simulation of natural gas in a study area by using a spreadsheet of Excel based on the activation energy, the mass fraction and the frequency factor of the light carbon methane, to obtain activation energy, a mass fraction and a frequency factor of heavy carbon methane.

In a specific example, since heavy carbon methane occupies a very small proportion in methane while light carbon methane occupies a very large proportion, these parameters are assumed to be the frequency factor and activation energy distribution of light carbon methane, and the calculation process includes:

S201: expand the activation energy and the mass fraction of the light carbon methane, and set expansion values as initial values of the activation energy and the mass fraction of heavy carbon methane.

S202: calculate a frequency factor of the heavy carbon methane according to the frequency factor of the light carbon methane, where the frequency factor of the heavy carbon methane is expressed as follows:

$$A^{13}C = 1.02 \times A^{12}C$$

where, $A^{13}C$ represents the frequency factor of the heavy carbon methane, and $A^{12}C$ represents the frequency factor of the light carbon methane.

S203, calculate conversion rates and reaction rates of total reaction light carbon methane and heavy carbon methane precursors by the activation energy, the mass fraction and the frequency factor of the light carbon methane and the initial values of the activation energy and mass fraction of the heavy carbon methane and the frequency factor thereof, including:

S2031, calculate reaction rate constants of all reaction light carbon methane and heavy carbon methane separately according to the activation energy, the mass fraction and the frequency factor of the light carbon methane and the initial values of the activation energy and the mass fraction of the heavy carbon methane as well as the frequency factor thereof.

S2032, calculate unreacted amounts of all reaction light carbon methane and heavy carbon methane precursors separately according to the activation energy, the mass fraction and the frequency factor of the light carbon methane and the initial values of the activation energy and the mass fraction of the heavy carbon methane as well as the frequency factor thereof.

S2033, calculate conversion rates of all the reaction light carbon methane and heavy carbon methane precursors separately according to the unreacted amounts of the light carbon methane and heavy carbon methane precursors; calculate reaction rates of all the reaction light carbon methane and heavy carbon methane precursors separately according to the conversion rates of the light carbon methane and heavy carbon methane precursors.

S2034, calculate conversion rates and reaction rates of the total reaction light carbon methane and heavy carbon methane precursors separately according to the conversion rates and reaction rates of all the reaction light carbon methane and heavy carbon methane precursors.

In a specific example, the entire parameter fitting process involves the following calculation formula:

The process of kerogen pyrolysis to methane is represented by a series of parallel first-order reactions, and the rate constant of each parallel first-order reaction follows a semi-quantitative Arrhenius equation:

$$k_i = A \exp(-Ea_i / RT)$$

where, t represents a temperature; R represents an ideal gas constant (J/mol/K); $k_i$ represents a reaction rate constant of i-th reaction light carbon methane or heavy carbon methane; i=1, ..., n, and n represents a total number of reactants; A represents the frequency factor of the light carbon methane or the heavy carbon methane; $Ea_i$ represents the activation energy (J/mol) of the light carbon methane or heavy carbon methane.

The experimental sample is type I kerogen, so it is further assumed that all parallel reaction methane precursors have the same initial carbon isotopic composition, and that each parallel reaction has the same frequency factor, and the activation energy is discretely distributed. The calculation is as follows:

$$w_i(t) = \exp\left[-\int_0^t k(t)dt\right]$$

where, $w_i(t)$ represents an unreacted amount of the i-th reaction light carbon methane or heavy carbon methane precursor at time t.

At a constant heating rate Hr, the above formula is expressed as:

$$w_i(t) = \exp\left[-\sum_t \Delta U_i(t)\right]$$

$$\Delta U_i(t) = [U_i(t) - U_i(t-1)] / Hr$$

$$U_i(t) = T(t)A\exp(-Ea_i/RT(t)) \times \left\{1 - \frac{[Ea_i/RT(t)]^2 + a_1[Ea_i/RT(t)] + a_2}{[Ea_i/RT(t)]^2 + b_1[Ea_i/RT(t)] + b_2}\right\}$$

where, $w_i(t)$ represents an unreacted amount of the i-th reaction light carbon methane or heavy carbon methane precursor at time t; $\Delta U_i(t)$ represents a cumulative amount of a light carbon methane or heavy carbon methane reaction product from time t to time t−1; Hr represents a constant heating rate; $U_i(t)$ represents an average cumulative amount of the light carbon methane or heavy carbon methane reaction product at time t; R represents an ideal gas constant; T represents a temperature; $k_i$ represents a reaction rate constant of the i-th reaction light carbon methane or heavy carbon methane; $Ea_i$ represents the activation energy of the light carbon methane or heavy carbon methane; $a_1$, $a_2$, $b_1$ and $b_2$ represent constants for calculating the cumulative amount of the light carbon methane or heavy carbon methane reaction product at time t, $a_1$=2.334733, $a_2$=0.250621, $b_1$=3.330657 and $b_2$=1.681534; then, the following formulas are derived:

$$F_i(t) = f_{oi}[1 - w_i(t)]$$

$$r_i(t) = k_i(t)[f_{oi} - F_i(t)]$$

where, $F_i(t)$ represents a conversion rate of the i-th reaction light carbon methane or heavy carbon methane precursor at time t; $f_{oi}$ represents a mass fraction of each reaction light carbon methane or heavy carbon methane; $w_i(t)$ represents an unreacted amount of the i-th reaction light carbon methane or heavy carbon methane precursor at time t; $r_i(t)$ represents a reaction rate of the i-th reaction light carbon methane or heavy carbon methane at time t; $k_i(t)$ represents a reaction rate constant of the i-th reaction light carbon methane or heavy carbon methane at time t.

Therefore, the sum of n parallel reactions is expressed as:

$$F^*(t) = \Sigma F_i(t)$$

$$F(t) = \Sigma F_i(t)$$

$$r^*(t) = \Sigma r_i(t)$$

$$r(t) = \Sigma r_i(t)$$

where, $F(t)$ and $F^*(t)$ represent the conversion rates of the total reaction heavy carbon methane and light carbon methane precursors at time t; $r(t)$ and $r^*(t)$ represent the reaction rates of the total reaction heavy carbon methane and light carbon methane precursors at time t; $F_i(t)$ represents the conversion rate of the i-th reaction light carbon methane or heavy carbon methane precursor at time t; $r_i(t)$ represents the reaction rate of the i-th reaction light carbon methane or heavy carbon methane at time t.

S204, calculate a carbon isotope cumulative amount according to the conversion rates and the reaction rates of the total reaction light carbon methane and heavy carbon methane precursors as well as the pyrolysis experiment data, where the carbon isotope cumulative amount is expressed as follows:

$$\delta^{13}C(t)=[R_0F(t)/F^*(t)/R_{std}-1]1000$$

$$R_0=(\delta^{13}C_0/1000+1)R_{std}$$

where, $\delta^{13}C(t)$ represents a carbon isotope cumulative amount at time t; $R_0$ represents an initial carbon isotope ratio of the methane precursors; $F(t)$ and $F^*(t)$ represent the conversion rates of the total reaction heavy carbon methane and light carbon methane precursors, respectively; $\delta^{13}C_0$ represents an initial carbon isotope amount; $R_{std}$ represents a standard ratio of Pee Dee Belemnite (PDB).

S205, set an activation energy difference ΔEa between the heavy carbon methane and the light carbon methane as a variable cell in a spreadsheet window of Excel.

S206, obtain a target value in the spreadsheet function according to a carbon isotope measured amount from the pyrolysis experiment and the carbon isotope cumulative amount, where the target value X is expressed as follows:

$$X=\Sigma_t|\delta^{13}C^*(t)-\delta^{13}C(t)|$$

where, $\delta^{13}C^*(t)$ represents a carbon isotope measured amount at time t, and $\delta^{13}C(t)$ represents a carbon isotope cumulative amount at time t.

S207, establish a constraint for obtaining the activation energy and mass fraction of the heavy carbon methane, specifically: a sum of the mass fractions $f_{oi}$ of all the reaction heavy carbon methane is set to 1, $f_{oi} \geq 0$, and a range of the activation energy difference ΔEa between the reaction heavy carbon methane and the light carbon methane is set to 80-250 J/mol.

S208, fit the target value by using a nonlinear interior point method of Excel according to the constraint; determine whether the target value is close to a preset limit value 0 during the fitting process; if yes, complete the fitting to obtain the activation energy, mass fraction and frequency factor of the heavy carbon methane; otherwise, return to step S205.

Figure 2:
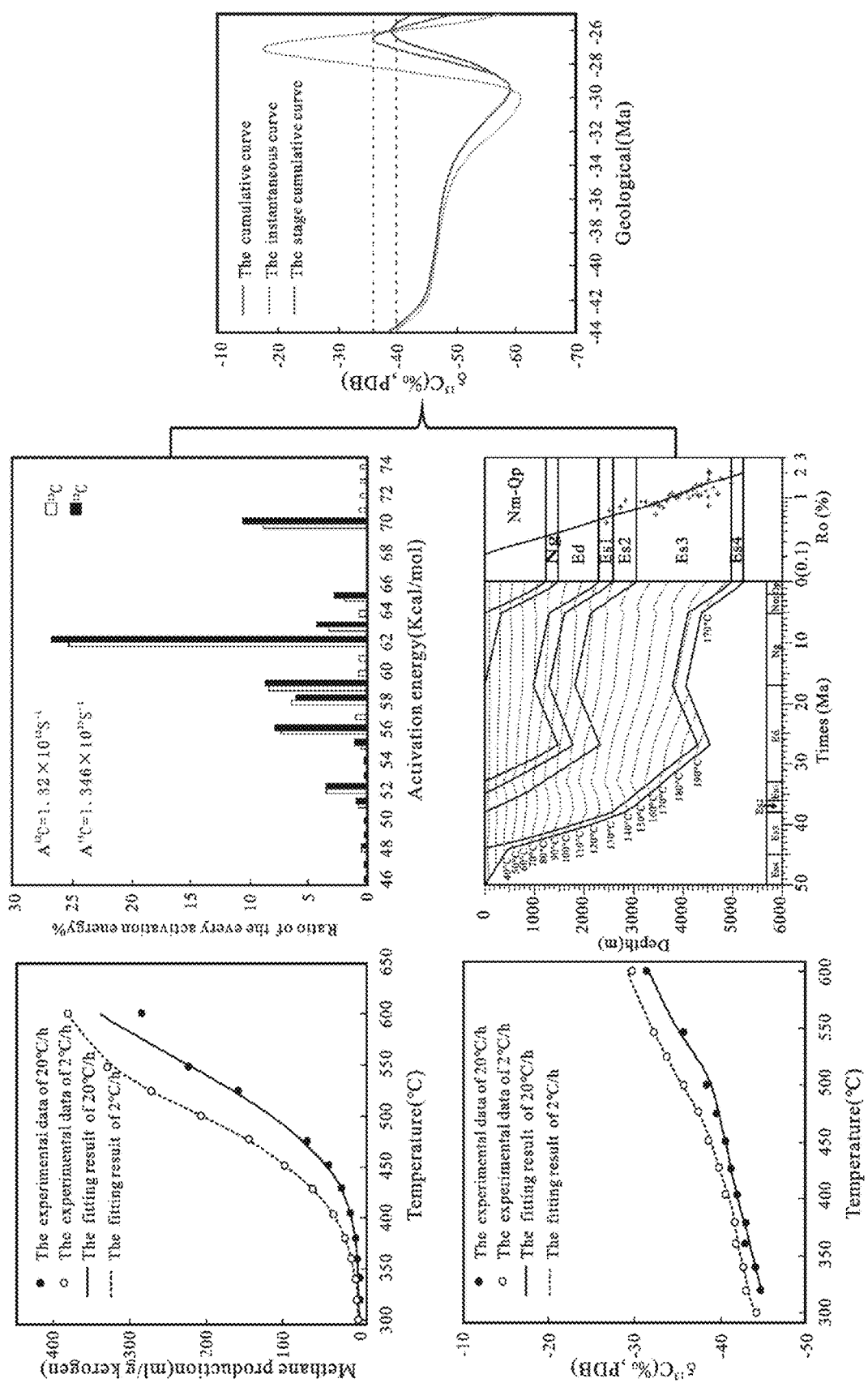
FIG. 2 shows an air source comparison between an instantaneous curve, a cumulative curve and a stage cumulative curve of natural gas and a carbon isotope measured amount as well as recovery of an accumulation history according to an example.

As shown in FIG. 2, in a specific example, the carbon isotope kinetics simulation of methane is conducted by using the spreadsheet function of Excel based on the carbon isotope amount measured by the pyrolysis experiment, to obtain the activation energy distribution and frequency factor of the heavy carbon methane. The parameter fitting is as follows:

The activation energy and mass fraction of the light carbon methane are expanded and assumed to be the initial values of the kinetic parameters of the heavy carbon methane. The above calculation formulas are entered into Excel, and the activation energy difference ΔEa between the heavy and light carbon methane is set as a variable cell. A function value of a sum of errors between the carbon isotope measured amount from the pyrolysis experiment and the calculated carbon isotope cumulative amount is set as a target value, and the target value is set to 0. Then the constraint of the calculation process is established. Finally, the activation energy difference ΔEa and the mass fraction are solved by using a nonlinear interior point method of Excel. The error is minimized through repeated adjustments, thereby obtaining the activation energy difference ΔEa. If the error of the fitted parameter is still large, the mass fraction is continuously adjusted by using the above fitting method until the fitting result is satisfactory and the error is minimized.

S3, establish a burial history and a thermal history of the study area based on geological data.

S4, combine the activation energy, the mass fraction and the frequency factor of the heavy carbon methane with the burial history and the thermal history of the study area to establish an instantaneous curve, a cumulative curve and a stage cumulative curve of the natural gas under geological conditions to form a history of natural gas accumulation, thereby completing the formation of the natural gas accumulation history by using carbon isotopes by the pyrolysis experiment.

The established cumulative curve of natural gas under geological conditions is expressed as follows:

$$\delta^{13}C(t)=[R_0F(t)/F^*(t)/R_{std}-1]1000$$

$$R_0=(\delta^{13}C_0/1000+1)R_{std}$$

where, $\delta^{13}C(t)$ represents a carbon isotope cumulative amount of natural gas under geological conditions at time t; $R_0$ represents an initial carbon isotope ratio of the methane precursors; $F(t)$ and $F^*(t)$ represent the conversion rates of the total reaction heavy carbon methane and light carbon methane precursors, respectively; $\delta^{13}C_0$ represents an initial carbon isotope amount; $R_{std}$ represents a standard ratio of PDB.

The established instantaneous curve of natural gas under geological conditions is expressed as follows:

$$\delta^{13}C_{inst}(t)=\{R_0\Sigma r_i(t)/\Sigma r_i^*(t) \times [1-F(t)]/[1-F^*(t)]/R_{std}-1\}1000$$

$$R_0=(\delta^{13}C_0/1000+1)R_{std}$$

where, $\delta^{13}C_{inst}(t)$ represents a carbon isotope instantaneous amount of natural gas under geological conditions at time t; $R_0$ represents an initial carbon isotope ratio of the methane precursors; $F(t)$ and $F^*(t)$ represent the conversion rates of the total reaction heavy carbon methane and light carbon methane precursors, respectively; $r_i(t)$ and $r_i^*(t)$ represent reaction rates of i-th reaction heavy carbon methane and light carbon methane precursors at time t; $\delta^{13}C_0$ represents an initial carbon isotope amount; $R_{std}$ represents a standard ratio of PDB.

The established stage cumulative curve of natural gas under geological conditions is expressed as follows:

$$\delta^{13}C_{step}(t)=\delta^{13}C_{inst}(t-1)\times\{[F(t)-F(t-1)]/[F^*(t)-F^*(t-1)]\}+\{[F(t)-F(t-1)]/[F^*(t)-F^*(t-1)]-1\}1000$$

where, $\delta^{13}C_{step}(t)$ represents a carbon isotope stage cumulative amount of natural gas under geological conditions at time t; $F(t)$ represents a conversion rate of the total reaction heavy carbon methane precursor at time t; $F^*(t)$ represents a conversion rate of the total reaction light carbon methane precursor.

Through the above design, the present invention provides a new way of recovering the history of natural gas accumulation, breaking the limitation of static models established only based on thermal simulation experimental data or measured carbon isotope data. The present invention improves the accuracy of the natural gas accumulation history, and applies to carbon isotope kinetics simulation of natural gas in a wide range of areas, making the natural gas accumulation history more authentic and reliable.

What is claimed is:
1. A method for forming a history of natural gas accumulation by using carbon isotopes by a pyrolysis experiment, comprising the following steps:
S1, performing a pyrolysis experiment on a selected kerogen sample to obtain activation energy, a mass fraction and a frequency factor of light carbon methane;

S2, carrying out carbon isotope kinetics simulation of natural gas in a study area based on the activation energy, the mass fraction and the frequency factor of the light carbon methane, to obtain activation energy, a mass fraction and a frequency factor of heavy carbon methane;

S3, establishing a burial history and a thermal history of the study area based on geological data; and S4, combining the activation energy, the mass fraction and the frequency factor of the heavy carbon methane with the burial history and the thermal history of the study area to obtain an instantaneous curve, a cumulative curve and a stage cumulative curve of the natural gas under geological conditions to form a history of natural gas accumulation;

wherein step S2 comprises the following steps:

S201: expanding the activation energy and the mass fraction of the light carbon methane, and setting expansion values as initial values of the activation energy and the mass fraction of heavy carbon methane;

S202: calculating a frequency of the heavy carbon methane according to the frequency factor of the light carbon methane, wherein the frequency factor of the heavy carbon methane is expressed as follows: $A^{13}C=1.02 \times A^{12}C$ wherein, $A^{13}C$ represents the frequency factor of the heavy carbon methane, and $A^{12}$ represents the frequency factor of the light carbon methane;

S203, calculating conversion rates and reaction rates of total reaction light carbon methane and heavy carbon methane precursors by the activation energy, the mass fraction and the frequency factor of the light carbon methane and the initial values of the activation energy and mass fraction of the heavy carbon methane and the frequency factor thereof;

S204, calculating a carbon isotope cumulative amount according to the conversion rates and the reaction rates of the total reaction light carbon methane and heavy carbon methane precursors as well as the pyrolysis experiment data, wherein the carbon isotope cumulative amount is expressed as: $\delta^{13}C(t)=[R_0 F(t)/F^*(t)/R_{std}-1]1000$, where $R_0=(\delta^{13}C_0/1000+1)R_{std}$, wherein $\delta^{13}C(t)$ represents a carbon isotope cumulative amount at time t; $R_0$ represents an initial carbon isotope ratio of the methane precursors; $F(t)$ and $F^*(t)$ represent the conversion rates of the total reaction heavy carbon methane and light carbon methane precursors, respectively; $\delta^{13}C_0$ represents an initial carbon isotope amount, $R_{std}$ represents a standard ratio of Pee Dee Belemnite (PDB);

S205, setting an activation energy difference $\Delta Ea$ between the heavy carbon methane and the light carbon methane as a variable value;

S206, obtaining a target value according to a carbon isotope measured amount from the pyrolysis experiment and the carbon isotope cumulative amount, wherein the target value X is expressed as follows: $X=\Sigma_t |\delta^{13}C^*(t)-\delta^{13}C(t)|$ wherein, $\delta^{13}C^*(t)$ represents a carbon isotope measured amount at time t, and $\delta^{13}C(t)$ represents a carbon isotope cumulative amount at time t;

S207, establishing a constraint for obtaining the activation energy and mass fraction of the heavy carbon methane; and S208, fitting the target value by using a nonlinear interior point method according to the constraint; determining whether the target value is close to a preset limit value 0 during the fitting process; if yes, completing the fitting to obtain the activation energy, mass fraction and frequency factor of the heavy carbon methane; otherwise, returning to step S205.

2. The method for forming a history of natural gas accumulation by using carbon isotopes by a pyrolysis experiment according to claim 1, wherein step S1 comprises the following steps:

S101, performing the pyrolysis experiment on the selected kerogen sample to obtain a pyrolysis product of the selected kerogen sample and a yield thereof; and S102, carrying out hydrocarbon generation kinetics analysis based on the pyrolysis product and the yield thereof, to obtain the activation energy, the mass fraction and the frequency factor of light carbon methane.

3. The method for forming a history of natural gas accumulation by using carbon isotopes by a pyrolysis experiment according to claim 1, wherein step S203 comprises the following steps:

S2031, calculating reaction rate constants of all reaction light carbon methane and heavy carbon methane separately according to the activation energy, the mass fraction and the frequency factor of the light carbon methane and the initial values of the activation energy and the mass fraction of the heavy carbon methane as well as the frequency factor thereof;

S2032, calculating unreacted amounts of all reaction light carbon methane and heavy carbon methane precursors separately according to the activation energy, the mass fraction and the frequency factor of the light carbon methane and the initial values of the activation energy and the mass fraction of the heavy carbon methane as well as the frequency factor thereof;

S2033, calculating conversion rates of all the reaction light carbon methane and heavy carbon methane precursors separately according to the unreacted amounts of the light carbon methane and heavy carbon methane precursors; calculating reaction rates of all the reaction light carbon methane and heavy carbon methane precursors separately according to the conversion rates of the light carbon methane and heavy carbon methane precursors;

S2034, calculating conversion rates and reaction rates of the total reaction light carbon methane and heavy carbon methane precursors separately according to the conversion rates and reaction rates of all the reaction light carbon methane and heavy carbon methane precursors.

4. The method for forming a history of natural gas accumulation by using carbon isotopes by a pyrolysis experiment according to claim 3, wherein in step S2031, the reaction rate constant of each reaction light carbon methane or heavy carbon methane is expressed as follows:

$$k_i = A \exp(-Ea_i/RT)$$

wherein, $Ea_i$ represents the activation energy of the light carbon methane or the heavy carbon methane; A represents the frequency factor of the light carbon methane or the heavy carbon methane; R represents an ideal gas constant; T represents a temperature; $k_i$ represents a reaction rate constant of i-th reaction light carbon methane or heavy carbon methane; i=1, . . . , n, and n represents a total number of reactants.

5. The method for forming a history of natural gas accumulation by using carbon isotopes by a pyrolysis experiment according to claim 3, wherein in step S2032, the unreacted amount of each reaction light carbon methane or heavy carbon methane precursor is expressed as follows:

$$w_i(t) = \exp\left[-\sum_t \Delta U_i(t)\right]$$

$$\Delta U_i(t) = [U_i(t) - U_i(t-1)]/Hr$$

$$U_i(t) = T(t)A\exp(-Ea_i/RT(t)) \times \left\{1 - \frac{[Ea_i/RT(t)]^2 + a_1[Ea_i/RT(t)] + a_2}{[Ea_i/RT(t)]^2 + b_1[Ea_i/RT(t)] + b_2}\right\}$$

wherein, $w_i(t)$ represents an unreacted amount of the i-th reaction light carbon methane or heavy carbon methane precursor at time t; $\Delta U_i(t)$ represents an average cumulative amount of a light carbon methane or heavy carbon methane reaction product from time t to time t−1; Hr represents a constant heating rate; $U_i(t)$ represents a cumulative amount of the light carbon methane or heavy carbon methane reaction product at time t; R represents an ideal gas constant; T represents a temperature; $k_i$ represents a reaction rate constant of the i-th reaction light carbon methane or heavy carbon methane; $Ea_i$ represents the activation energy of the light carbon methane or heavy carbon methane; $a_1$, $a_2$, $b_1$ and $b_2$ represent constants for calculating the cumulative amount of the light carbon methane or heavy carbon methane reaction product at time t, $a_1$=2.334733, $a_2$=0.250621, $b_1$=3.330657 and $b_2$=1.681534.

6. The method for forming a history of natural gas accumulation by using carbon isotopes by a pyrolysis experiment according to claim 3, wherein in step S2033, the conversion rate of each reaction light carbon methane or heavy carbon methane precursor is expressed as follows:

$$F_i(t)=f_{oi}[1-w_i(t)]$$

the reaction rate of each reaction light carbon methane or heavy carbon methane precursor is expressed as follows:

$$r_i(t)=k_i(t)[f_{oi}-F_i(t)]$$

wherein, $F_i(t)$ represents a conversion rate of the i-th reaction light carbon methane or heavy carbon methane precursor at time t; $f_{oi}$ represents a mass fraction of each reaction light carbon methane or heavy carbon methane; $w_i(t)$ represents an unreacted amount of the i-th reaction light carbon methane or heavy carbon methane precursor at time t; $r_i(t)$ represents a reaction rate of the i-th reaction light carbon methane or heavy carbon methane at time t; $k_i(t)$ represents a reaction rate constant of the i-th reaction light carbon methane or heavy carbon methane at time t.

7. The method for forming a history of natural gas accumulation by using carbon isotopes by a pyrolysis experiment according to claim 3, wherein in step S2034, the conversion rate of the total reaction light carbon methane or heavy carbon methane precursor is expressed as follows:

$$F^*(t)=\Sigma F_i(t)$$

$$F(t)=\Sigma F_i(t)$$

the reaction rate of the total reaction light carbon methane or heavy carbon methane precursor is expressed as follows:

$$r^*(t)=\Sigma r_i(t)$$

$$r(t)=\Sigma r_i(t)$$

wherein, F(t) and F*(t) represent the conversion rates of the total reaction heavy carbon methane and light carbon methane precursors at time t; r(t) and r*(t) represent the reaction rates of the total reaction heavy carbon methane and light carbon methane precursors at time t; $F_i(t)$ represents the conversion rate of the i-th reaction light carbon methane or heavy carbon methane precursor at time t; $r_i(t)$ represents the reaction rate of the i-th reaction light carbon methane or heavy carbon methane at time t.

8. The method for forming a history of natural gas accumulation by using carbon isotopes by a pyrolysis experiment according to claim 1, wherein in step S207, the constraint is:
a sum of the mass fractions $f_{oi}$ of all the reaction heavy carbon methane is set to 1, $f_{oi} \geq 0$, and a range of the activation energy difference ΔEa between the reaction heavy carbon methane and the light carbon methane is set to 80-250 J/mol.

9. The method for forming a history of natural gas accumulation by using carbon isotopes by a pyrolysis experiment according to claim 1, wherein in step S4, the established cumulative curve of natural gas under geological conditions is expressed as follows:

$$\delta^{13}C(t)=[R_0F(t)/F^*(t)/R_{std}-1]1000$$

$$R_0=(\delta^{13}C_0/1000+1)R_{std}$$

wherein, $\delta^{13}C_{cum}(t)$ represents a carbon isotope cumulative amount of natural gas under geological conditions at time t; $R_0$ represents an initial carbon isotope ratio of the methane precursors; F(t) and F*(t) represent the conversion rates of the total reaction heavy carbon methane and light carbon methane precursors, respectively; $\delta^{13}C_0$ represents an initial carbon isotope amount; $R_{std}$ represents a standard ratio of PDB;
the established instantaneous curve of natural gas under geological conditions is expressed as follows:

$$\delta^{13}C_{inst}(t)=\{R_0\Sigma r_i(t)/\Sigma r_i^*(t)\times[1-F(t)]/[1-F^*(t)]/R_{std}-1\}1000$$

$$R_0=(\delta^{13}C_0/1000+1)R_{std}$$

wherein, $\delta^{13}C_{inst}(t)$ represents a carbon isotope instantaneous amount of natural gas under geological conditions at time t; $R_0$ represents an initial carbon isotope ratio of the methane precursors; F(t) and F*(t) represent the conversion rates of the total reaction heavy carbon methane and light carbon methane precursors, respectively; $r_i(t)$ and $r_i^*(t)$ represent reaction rates of i-th reaction heavy carbon methane and light carbon methane precursors at time t; $\delta^{13}C_0$ represents an initial carbon isotope amount; $R_{std}$ represents a standard ratio of PDB;
the established stage cumulative curve of natural gas under geological conditions is expressed as follows:

$$\delta^{13}C_{step}(t)=\delta^{13}C_{inst}(t-1)\times\{[F(t)-F(t-1)]/[F^*(t)-F^*(t-1)]\}+\{[F(t)-F(t-1)]/[F^*(t)-F^*(t-1)]-1\}1000$$

wherein, $\delta^{13}C_{step}(t)$ represents a carbon isotope stage cumulative amount of natural gas under geological conditions at time t; F(t) represents a conversion rate of the total reaction heavy carbon methane precursor at time t; F*(t) represents a conversion rate of the total reaction light carbon methane precursor.

\* \* \* \* \*